United States Patent [19]

Howard et al.

[11] Patent Number: 5,024,519
[45] Date of Patent: Jun. 18, 1991

[54] APPARATUS AND METHOD FOR VISUAL-FIELD TESTING

[75] Inventors: Dwight L. Howard, Winters; Chris A. Johnson, Davis, both of Calif.

[73] Assignee: Regents of the University of California, Oakland, Calif.

[21] Appl. No.: 482,278

[22] Filed: Feb. 20, 1990

[51] Int. Cl.$^5$ .............................................. A61B 3/02
[52] U.S. Cl. ..................................... 351/226; 351/224
[58] Field of Search ............... 351/203, 219, 222, 223, 351/224, 226

[56] References Cited

U.S. PATENT DOCUMENTS 4,169,664 10/1979 Bailey, Jr. ........................... 351/226
4,871,247 10/1989 Haynes ................................. 351/226

OTHER PUBLICATIONS

Heijl, A., Computer Test Logics for Automated Perimetry, Acta Ophthalmologica 55:837 (1977).
Johnson, C. A. et al., "A Comparison of MOBS (Modified Binary Search) and Staircase Test Procedures in Automated Perimetry", *Noninvasive Assessment of the Visual System*, 1989 Technical Digest Series, 7:84 (1989).
Johnson, C. A., "The Test Logic of Automated Perimetry", Acta: XXIV International Congress of Ophthalmology, Henkind, P., Editor, pp. 151-155 (Philadelphia, J. B. Lippincott, 1983).
Johnson, C. A. et al., "Incidence of Visual Field Loss in 20,000 Eyes and its Relationship to Driving Performance", Arch. Ophthalmol., vol. 101, pp. 371-375 (1983).
Keltner, J. L. et al., Comparative Material on Automated and Semi-Automated Perimeters, *Ophthalmology*, vol. 93, pp. 1-25 (1986).
Lewis, R. A. et al., "Preliminary Clinical Trials with the Humphrey Field Analyzer", *Doc. Ophthalmol. Proc. Ser.*, vol. 42, pp. 159-165 (1985).
Shapiro, L. R. et al., "KRAKEN: A Computer Simulation Procedure for Static, Kinetic, Suprathreshold Static and Heuristic Perimetry", in *Perimetry Update 1988/1989: Proceedings of the VIIIth International Perimetry Society Meeting*, A. Heijl, Editor, (Amsterdam, Kugler Ghedini, 1989), pp. 431-438.
Tyrell, R. A. et al., "A Rapid Technique to Assess the Resting State of the Eyes and Other Threshold Phenomena: The Modified Binary Search (MOBS)", *Behavior Research Methods, Instruments, & Computers*, 20:137 (1988).

Primary Examiner—Paul M. Dzierzynski
Attorney, Agent, or Firm—Peter J. Dehlinger

[57] ABSTRACT

Apparatus and method for visual-field testing. The apparatus includes an ocular device which fits over a subject's eye and which has a cavity-like inner surface dimensioned to encompass the subject's visual field. The ocular device is constructed to provide a background glow against which a fixed light image and a series of transient, different-position light image in the subject's visual field can be perceived. The images are preferably formed by a Badal-optical system which allows the images to be perceived without the need for corrective lenses. Also disclosed is a tandem-optics system for coordinately focusing fixed- and movable-position light image assemblies.

20 Claims, 6 Drawing Sheets

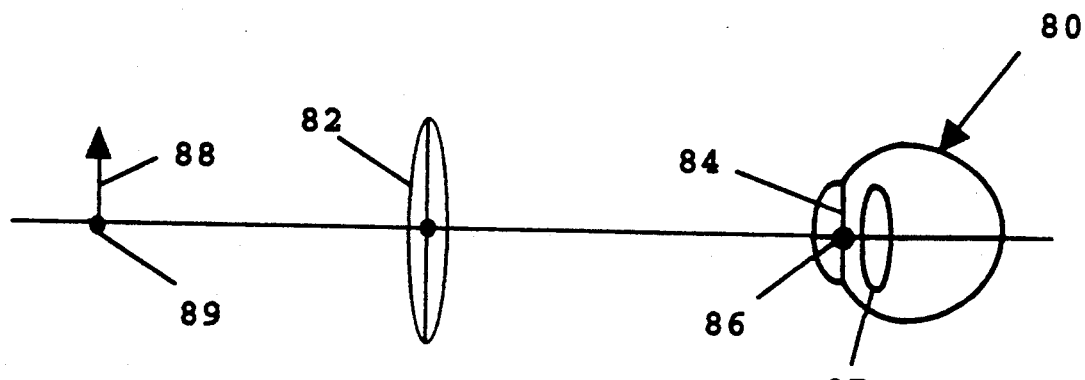
Fig. 4
Fig. 5
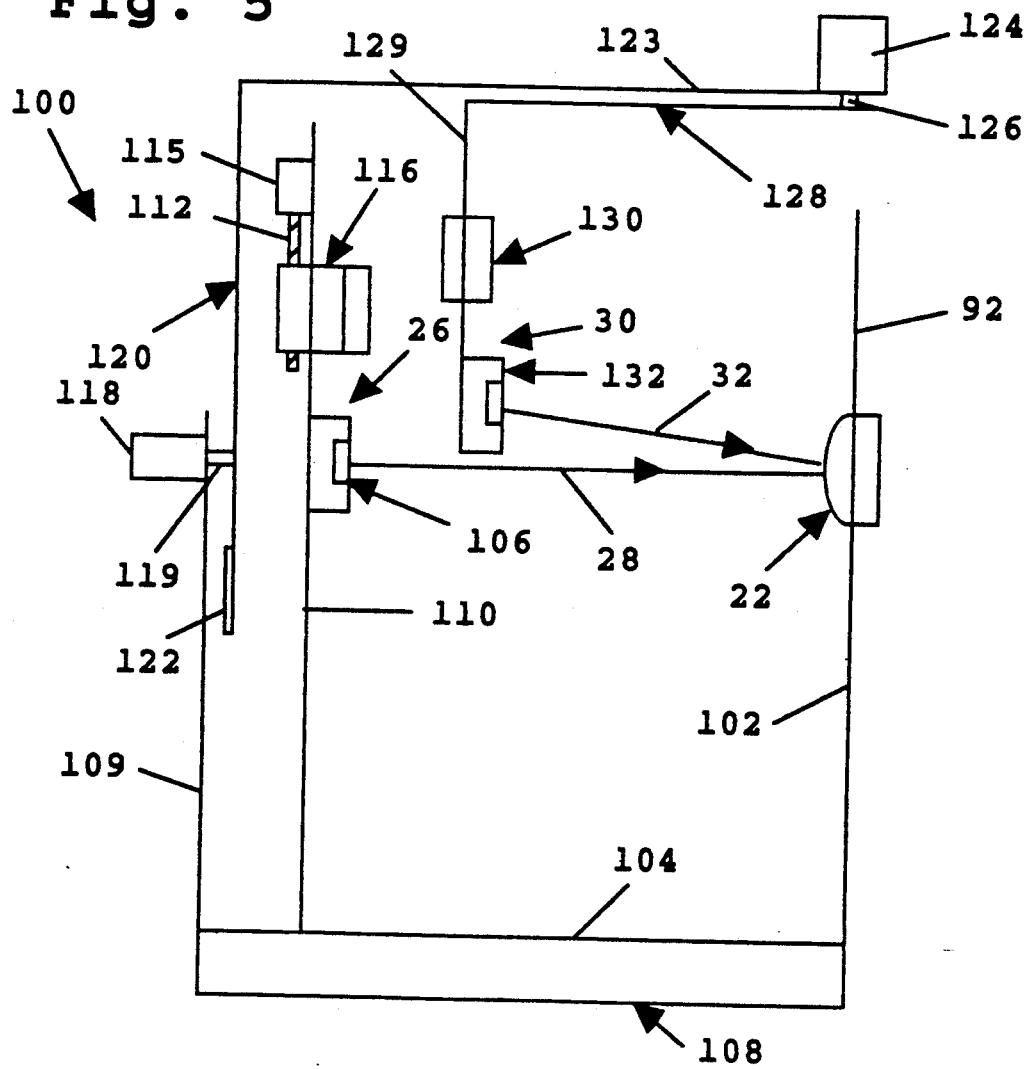

APPARATUS AND METHOD FOR VISUAL-FIELD TESTING

FIELD OF THE INVENTION

The present invention relates to an apparatus and method for use in visual-field testing, in particular, for testing the range and sensitivity of a subject's visual field.

REFERENCES

Anderson, D. R., *Perimetry With and Without Automation*, C. V. Mosby, St. Louis, 1987.

Heijl A: Computer test logics for automated perimetry. Acta Ophthalmologica 55:837, 1977.

Johnson, C. A. and Shapiro, L. R.: "A Comparison of MOBS (Modified Binary Search) and Staircase Test Procedures in Automated Perimetry". *Noninvasive Assessment of the Visual system*, 1989 *Technical digest Series* 7:84, 1989.

Johnson C. A.: "The Test Logic of Automated Perimetry". In Acta: *XXIV International Congress of Ophthalmology*, Henkind P. editor. Philadelphia, J. B. Lippincott, 1983, pp. 151-155.

Johnson, C. A., Keltner, J. L., "Incidence Of Visual Field Loss in 20,000 Eyes and its Relationship to Driving Performance", *Arch. Opthalmol.*, vol. 101, pages 371-375, 1983.

Keltner, J. L., Johnson, C. A., "Comparative Material on Automated and Semi Automated Perimeters", *Ophthalmology*, vol. 93, pages 1-25, 1986.

Lewis, R. A., et al., "Preliminary Clinical Trials With the Humphrey Field Analyzer", *Doc. Opthalmol. Proc. Ser.*, vol. 42, pages 159-165, 1985.

Shapiro L. R., Johnson C. A., and Kennedy R. L.: "KRAKEN: A Computer Simulation Procedure for Static, Kinetic, Suprathreshold Static and Heuristic Perimetry." In *Perimetry Update* 1988/89: *Proceedings of the VIIIth International Perimetry Society Meeting*, Heijl A., editor. Amsterdam, Kugler & Ghedini, 1989, pp. 431-438.

Tyrell, R. A. and Owens, D. A.: "A Rapid Technique to Assess the Resting States of the Eyes and Other Threshold Phenomena: The Modified Binary Search (MOBS)". *Behavior Research Methods, Instruments, & Computers* 20:137, 1988.

BACKGROUND OF THE INVENTION

Ophthalmic tests to determine the range and sensitivity of a subject's visual field are commonly performed (Anderson 1987, Johnson, 1983a). Many diseases of the eye, e.g., glaucoma and optic neuropathies, affect field of vision, and often these diseases are evidenced at an early stage, when treatment may be most effective, by reduction in visual field sensitivity. Additionally, the type and extent of many eye diseases, and the location of the disease along the visual pathway (i.e. the eye, the optic nerve, or the visual centers of the brain) can often be determined by visual field examination.

Presently there are a number of commercially-available visual field analyzers. The most widely used is the Humphrey Field Analyzer (Allergan Humphrey, Inc.). This device is a projection-type analyzer which performs static and suprathreshold static testing of the central and peripheral visual field (Lewis). Non-projection visual field analyzers are also used, although these analyzers have more limited capabilities than projection analyzers. Both type of analyzers are relatively expensive and non-portable.

In addition, the above analyzers require near-sighted or far-sighted users to wear corrective lenses, since a sharp focus is necessary for accurate testing. Also, during the examination, the user's head must be placed on a chin rest for an extended examination periods, e.g., up to a half-hour. This requirement may hinder testing due to artifacts introduced by the motion of the user to relieve discomfort.

SUMMARY OF THE INVENTION

It is therefore one general object of the invention to provide a portable, low-cost apparatus for testing a subject's visual field.

In one aspect, the invention includes an apparatus for measuring a subject's response to a light stimulus, over the subject's visual field. The apparatus includes an ocular device which is placed over, i.e. against, a subject's eye. The device has a transparent window defining an outwardly projecting, cavity-like inner surface dimensioned to encompass the subject's field of vision in that eye. Also included in the apparatus is an optical system for producing a fixed-position image at one position in the user's visual field, and a series of transient images at different selected positions in the subject's visual field.

The ocular device is designed, in accordance with the invention to provide a substantially uniform glow on the inner surface of the eyepiece window against which the fixed position and transient images can be perceived.

In a preferred embodiment of the invention, the optical system is a Badal-type system designed to provide focused fixed position and transient light images over a range of $-6$ to $+6$ diopters, without the requirement of corrective lenses.

In another embodiment the invention includes a tandem optical system designed to focus both the fixed and movable images with a single focusing operation. The optical system includes a frame arm and a stimulus arm to which are attached a fixed-image assembly and a movable-image assembly, respectively. The stimulus arm is capable of being positioned in three dimensions at a fixed distance from the user. Each image assembly includes a light source and a focusing structure. The movable image assembly further includes a brake mechanism which is released by a coupling device, associated with the fixed-image assembly, for moving the two focusing structures coordinately.

These and other objects and features of the invention will become more fully apparent when the following detailed description is read in conjunction with the accompanying drawings.

BRIEF DESCRIPTION OF THE DRAWINGS

FIG. 4 illustrates the principles of a Badal-type optic system.

FIG. 5 is a side view of the apparatus of the invention, showing particularly a Badal-type optical system employed in the apparatus.

FIG. 9A shows a side view of the coupling device and the brake immediately before or after engagement. FIG. 9B shows the coupling device and brake during engagement.

DETAILED DESCRIPTION OF THE INVENTION

Figure 1:
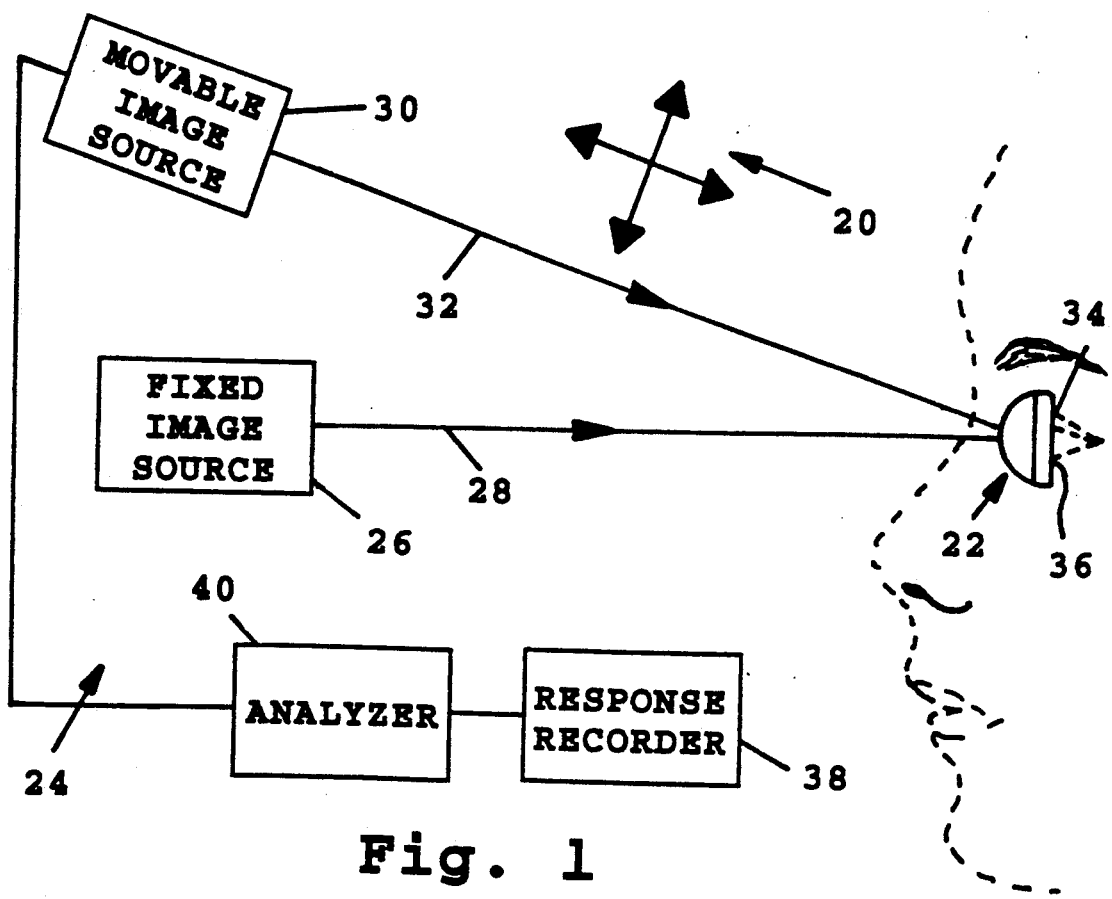
FIG. 1 shows, in schematic view, the apparatus of the invention, including an ocular device, an optical system for projecting fixed and selected-position images against the subject's retina, and a recording device.

FIG. 1 illustrates, in schematic view, an apparatus for measuring a subject's visual field in accordance with the invention. The apparatus includes an ocular device 22 adapted to be placed over a subject's eye, as shown. An optical system 24 in the apparatus includes a fixed-image light assembly 26, for producing a fixed-position image along a path 28 through the central region of the ocular device, and a movable-image light assembly 30, designed to be positioned at any point within the subject's visual field, to project a transient light stimulus to the subject's eye along a path 32. During the course of visual-field testing, the movable-image light assembly is used to produce a series of transient images over the visual field of the subject.

The apparatus further includes illumination means, including light sources 34, 36, to provide a uniformly lighted background glow within the ocular device. The ocular device and illuminating means are described in Section A and the optical system, in Section B. The apparatus may further include a recorder 38 for recording the subject's responses to the light stimuli, and an analyzer 40 for controlling the position of the movable-image light assembly, as described in Section C.

A. OCULAR DEVICE

Figure 2:
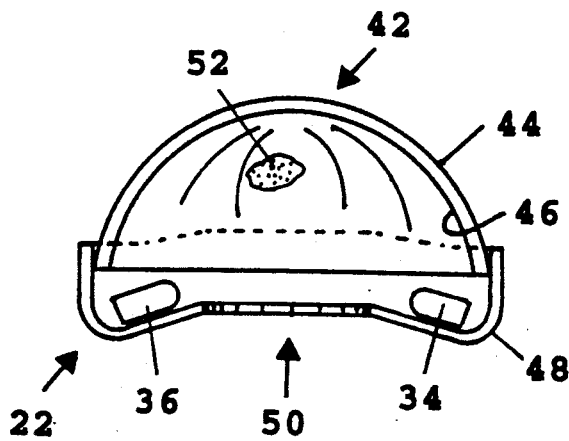
FIG. 2 shows a top view of an ocular device constructed according to one embodiment of the invention.

FIG. 2 shows the top view of ocular device 22 constructed in accordance with one embodiment of the present invention. The device includes a preferably hemispherical transparent window 42 having inner and outer surfaces 46, 44, respectively. More particularly, the window defines an outwardly bulging, cavity-like inner surface 46 dimensioned to encompass the user's field of vision when the ocular device is placed against the user's eye as shown in FIG. 1. The window is bordered by a rim 48 which is designed to be placed against a user's eye to block stray light from reaching the eye. The rim has a central aperture 50 through which the inner surface of the circular device is viewed, with the rim placed against the socket region of the eye. An aperture diameter of about 11/16 of an inch is acceptable for this purpose.

Window 42 is constructed from an optically-transparent, preferably lightweight material, such as acrylic, which can be formed into a preferably hemispherical shape. The ocular device should be dimensioned to be small, yet encompass the visual field of the subject's eye and be comfortable when the eye is placed against the rim. A rim diameter of between about 1 and 1.6 inches and a hemispherical surface diameter of between about 1 and 1.5 inches are suitable for these requirements.

Also shown in FIG. 2 is illumination means for illuminating the inner surface of the window, to provide a substantially uniform glow on the inner surface of the device. In one embodiment, exemplified by device 22, the illuminating means includes (a) a light source for directing light against the inner surface of the window and (b), a substantially uniform-surface distribution of speckle-like reflective material on the window. The uniform glow is produced when the reflective material is illuminated by the light source.

The light scattering properties of the reflective material are preferably such as to provide a highly uniform diffuse reflection, which reduces biasing effects due to stray light, and scattered light from the transient stimulus source. Further, the size and density of reflective particles must be such as to leave the window transparent for perceiving images from light sources 26, 30 when the surface is illuminated. These objectives can be accomplished by minimizing the edge dimension of the reflective particles to their reflective area while maintaining a uniform distribution of background light within the device.

One preferred reflective coating is produced by applying, e.g., with an air brush, a white paint mist to the interior surface. The spot size of mist particles on the window are preferably about 0.01 inches in diameter, and at a density which covers about 50% of the inner surface. Such reflective spots or particles are shown at 52 in FIG. 2.

Figure 3:
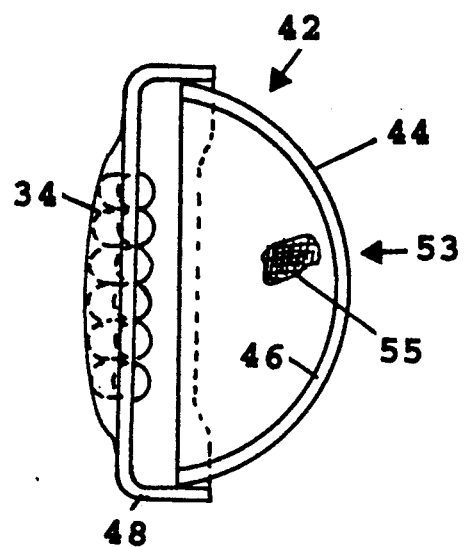
FIG. 3 is a side view of the FIG. 2 ocular device.

In another specific embodiment, the reflective surface is provided by a screen shown fragmentarily at 53 in FIG. 3, having a preferred mesh size of about 5-50 mils. It will be appreciated the screen may be placed against a transparent window, or may itself form the window. In the latter embodiment, the window may be thought of as an opaque window having a regular array of holes such as holes 55, which make the window transparent when it is placed against (close to) the eye.

The intensity of the background luminance is a critical parameter for clinical application of the invention. Determination of a subject's visual field using too dark a background may cause unstable readings, since the eye will become dark-adapted. Also, light levels which are too low often lead to spurious readings due to scattering of the transient stimulus light, especially in older individuals. On the other hand, if the background is too bright, light-scattering effects may also lead to spurious results. Additionally, a background light intensity which is too strong tends to cause discomfort in older individuals. A constant background light intensity of between about 5-15, and more preferably about 10 candela/$m^2$ is considered optimal for most types of visual field perimetry.

The light source in the illuminating means is provided by one or more light emitting diodes such as diodes 34, 36 (FIG. 2) located inside the ocular device. The LEDs should be arranged within the ocular device so that a substantially uniform glow is provided which will allow the light stimuli projected to the user's eye to be clearly visible, as described below. It has been found that commercially-available LEDs have adequate luminescence properties for such background illumination purposes.

FIGS. 2 and 3 show the placement of the LEDs in one preferred embodiment of the invention. Typically eight to ten LEDs are arranged in pods on opposite sides of the device, as shown. The LEDs are connected to any typical LED power source (the wiring and the power source are not shown) which provides constant selected voltage, and preferably at a voltage level sufficient to produce a level of light intensity between about 5-15 candela/$m^2$ within the ocular device. Typically, a short piece of copper wire extends form the cathode of each LED to the outer surface of the ocular device to dissipate heat generated by the LEDs.

Alternatively, the LEDs may be mounted on a metallic, e.g. aluminum, rim which forms part of a continuous metallic faceplate. The portion of the rim and faceplate which contacts the subject may be covered with plastic to provide comfort during use. This type of arrangement removes the need for LED pods and additional means of heat removal.

Another alternative light source for background illumination may include optical fibers whose ends are arranged within the ocular device to illuminate the inner surface of the ocular device as described above.

The use of optical fibers offers three advantages. First, the level of brightness available through the use of a external light source is much greater than with LEDs. Hence fewer optical fibers are required for illumination compared to the number of LEDs. Second, the use of color filters at the light source allows the color of the background light transmitted by the fiber optic wires to be varied. This offers greater flexibility in adapting the invention to perform clinical examinations. Third, using optical fibers for internal illumination removes the need for the LED pods and allow the user's eye to be placed closer to the rim of the ocular device.

In yet another embodiment, the illuminating means is provided by a fluorescent or phosphorescent compound embedded in or applied to the transparent window. The compound concentration is such that irradiation of the window by a suitable wavelength light induces fluorescence or phosphorescence at a level which produces the desired glow at the inner surface of the window.

In yet another embodiment, the window in the ocular device can be constructed to include high-voltage terminals and an ionizable gas in a jacket to produce a uniform background glow surrounding the transparent window.

B. OPTICAL SYSTEM

The movable-position light image assembly in the optical system is designed to produce transient images perceived by the subject, at selected locations in the subject's visual field, while the subject's focus is fixed on the fixed-position image. According to an important feature of the invention, the fixed-position and transient images are projected through the transparent window of the ocular and observed as focused images against the uniform glow produced at the inner surface of the ocular device, described above. This is possible because the subject's eye is too close to the window of the ocular device to focus on the reflective material which produces the glow on the window's inner surface. The subject can only perceive the diffusely reflected light from the internal illumination sources as a uniform background glow. However, the subject can clearly focus on the fixed-position and movable images which are beyond the window of the ocular device. Thus, these images are clearly seen against the background glow provided by the internal illumination means.

In one preferred embodiment of the invention, the optical system used for generating the fixed-position and transient images is a Badal-type optical system which eliminates the need for the subject to wear corrective lenses in order to focus on the transient images.

The basic operation of the Badal-type system is illustrated in FIG. 4. The subject's eye 80 is positioned with respect to Badal lens 82 such that the pupil 84 of the eye is located at the posterior focal point 86 of the Badal lens (in front of the subject's eye lens 87). Any positive (converging) lens can serve as the Badal lens; however, the posterior focal point of the lens must be placed at the subject's pupil for the images to be correctly focused.

An object 88 located at the anterior focal point 89 of the Badal lens will appear at optical infinity, and sharply focused, if the subject has normal vision. For subjects who are nearsighted (myopic) or farsighted (hyperopic), the same results are achieved by moving the object toward or away from the Badal lens respectively. The degree of myopia or hyperopia which can be compensated by the Badal system depends on the power of the lens and the available distance over which the object can be moved.

One preferred embodiment of a Badal-type optical system for use in the present invention is shown generally at 100 in FIG. 5. The figure shows a face plate 92, designed to shield the subject from stray light. Ocular device 22 is affixed to the face plate, which in turn is connected to supporting frame 108 in the optical system through supports 102, 104, as shown.

The fixed-position image assembly, here indicated generally at 26, is attached to frame 108 through a frame arm or post 110. The assembly projects a fixed-position image along path 20. Assembly 26 includes a image projector 106 rigidly attached to post 110, and a mirror assembly 116 which is slidably mounted on post 110 for positioning at a selected position above projector 106. The mirror assembly is operatively connected by a worm drive 112 to a stepper motor 115 attached to post 110 for controlling the movement of the mirror assembly on the post.

Also carried on frame 108, on a frame post 109, is a meridian drive motor 118, which is preferably a d.c. gear-motor using quadrature feedback designed to rotate its drive shaft 119 through a selected angle in response to signals supplied to the motor. Drive shaft 119 is attached to and rotates a primary angled arm 120 which has a counterweight 122 at its lower end in the figure to balance to weight of the secondary-arm structure now to be described.

Arm 120 extends at a right angle, providing an end segment 123 on which is attached a radial drive motor 124. The motor's drive shaft, indicated at 126, is attached to and rotates a secondary angled arm 128 also having angled end section 129, as shown. Motor 124 is preferably a d.c. motor which, like motor 118, is responsive to control signals supplied from a control unit. The primary and secondary arms in the movable-image assembly are also referred to herein collectively as a stimulus arm.

The movable-position image assembly in the system, here indicated generally at 30, includes an image projector 132 rigidly carried on the end of section 129, and a mirror assembly 130 which is slidably attached to section 129 for positioning a selected distance from projector 132, as described below. The operation of the two above-described image assemblies will be described below with reference to FIGS. 6 and 7.

The general mechanical operation of the optical system, to position an image from the movable-position image assembly at any position in the subject's visual field, can be appreciated from FIG. 5. Motor 118 is designed to swing primary arm 120 through a 270° arc, the lower 90° of arc being reserved for the subject's chin (45° to either side of the center of the chin). The radial drive motor, which is attached to the primary arm and moves therewith, is capable of moving secondary arm 128 through an arc of 70° to either side of the center of the hemispherical surface which is defined by the 360° movement of arm 120 and the 180° movement of arm 128. The stimulus arm construction is such that the hemispherical surface just mentioned has a radius of preferably between about 10-20 inches. The movement of the two motors is controlled by a control unit which is designed to output d.c. signals to the two motors to achieve the desired placement of the movable-image assembly.

Figure 6:
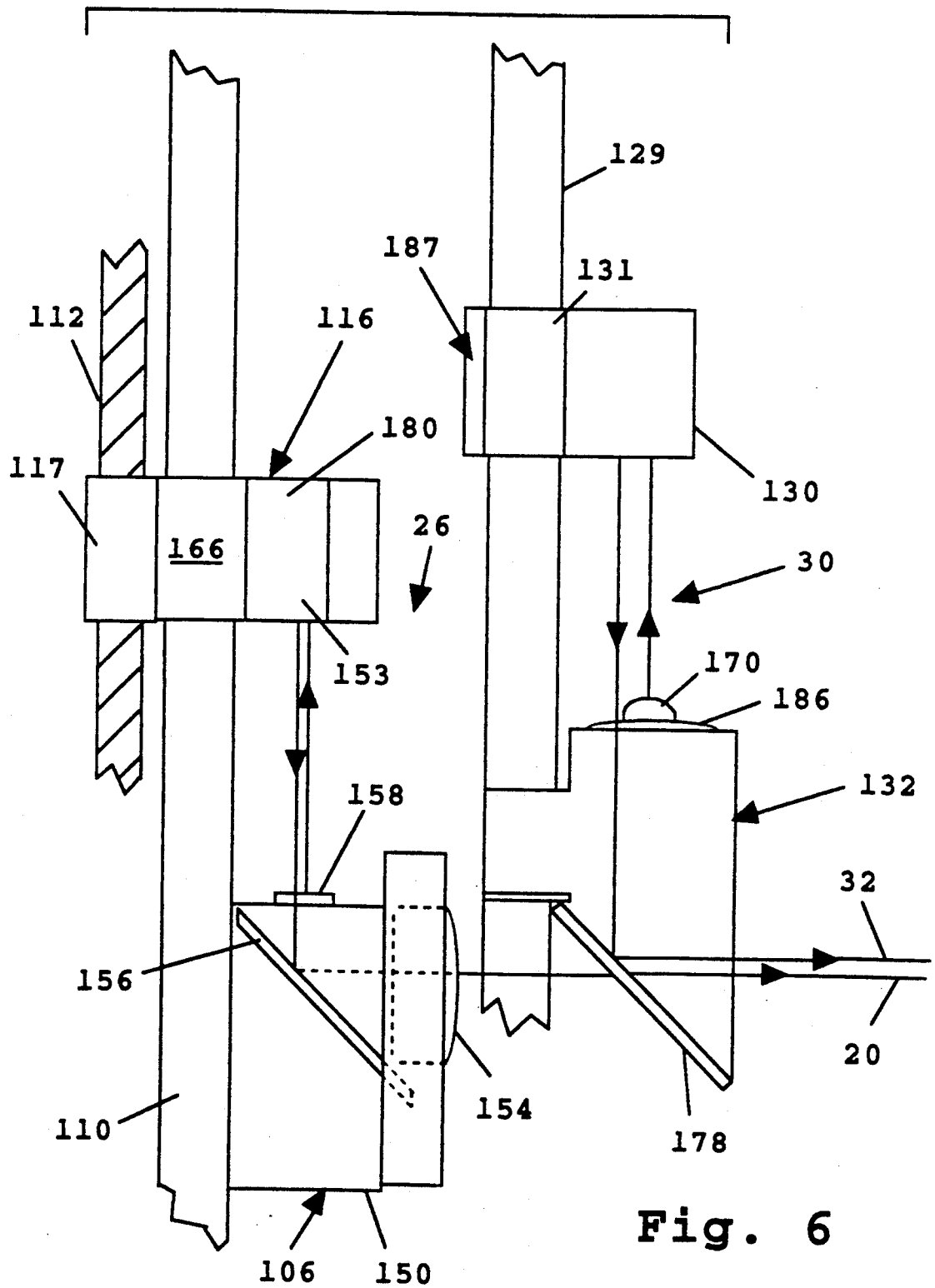
FIGS. 6 and 7 are side and front views, respectively, of the fixed-position and movable-position image assemblies shown in FIG. 5.
Figure 7:
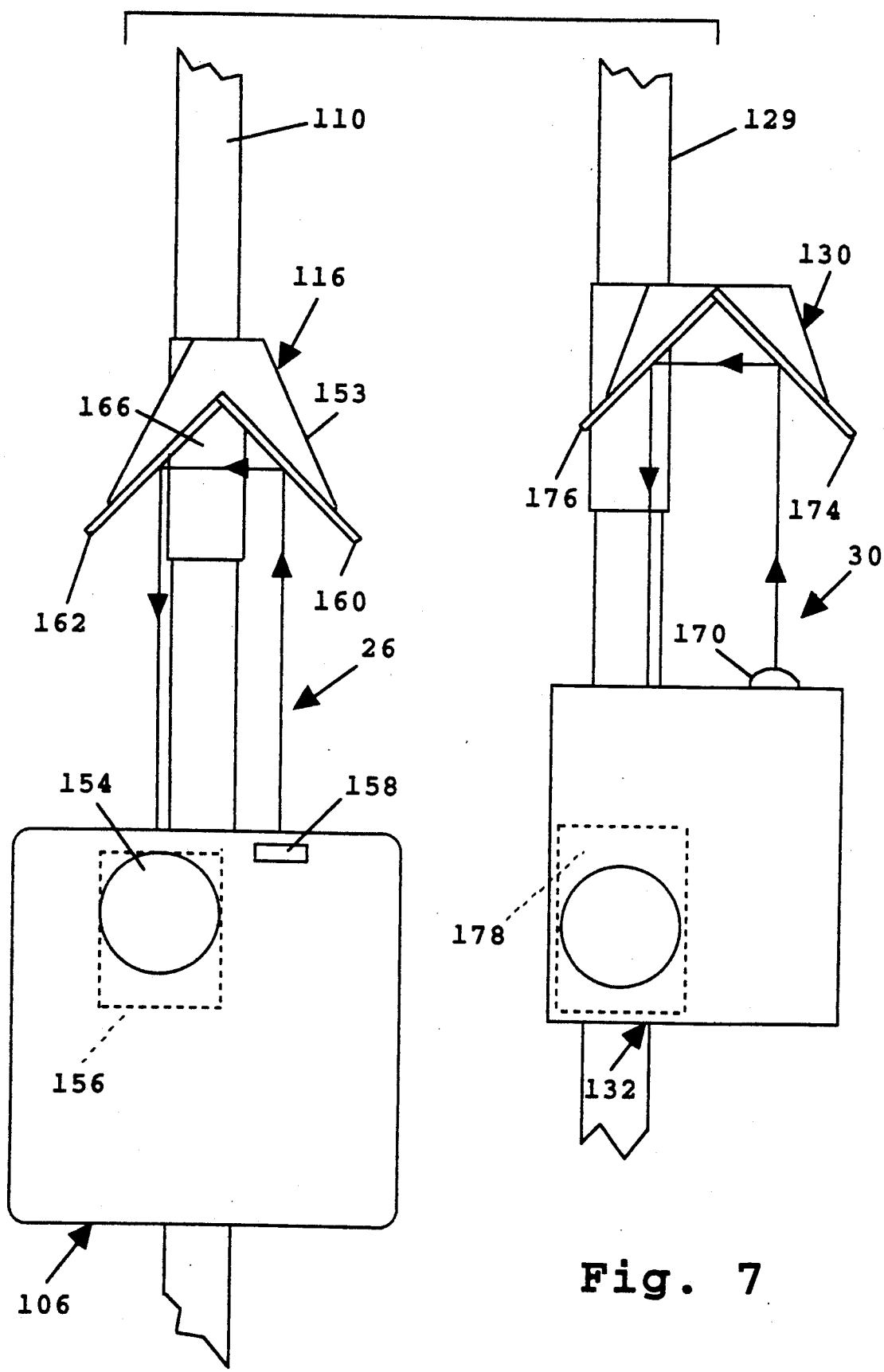

FIGS. 6 and 7 show side and front views of the two image assemblies, respectively. The construction and operation of the fixed-position assembly 26, shown at the left in the two figures, will be described first. Projector 106 attached to post 110 includes a light-tight housing 150 which contains a Badal lens 154, a mirror 156, mounted at a 45° angle from the vertical, and a light source 158. One preferred light source is a light-emitting diode (LED) and particularly an LED having the construction detailed below.

The image from the projector is produced by a slide transparency placed over the LED. The transparency has a pattern of cross-hairs superimposed over concentric circles, and the image formed thus has the appearance of a gun sight. Other patterns are suitable.

Mirror assembly 116 in the fixed-image assembly includes a housing 153 which is mounted on post 110 by a sleeve 166, for adjustable positioning on the arm. Sleeve 166 in turn is attached to a threaded sleeve 117 in which the worm screw of the above-described worm drive system is received. With reference to FIG. 7, the mirror assembly includes a pair of mirrors 160, 162 positioned at right angles to one another, and at 45° off vertical, as show. The two mirrors are positioned with respect to the projector components so that image from the light source 158 is (a) directed against mirror 160, and (b) reflected to mirror 162 and to mirror 156 in the projector. Mirror 156 in turn directs the image through lens 154 along path 20 to the center region of the ocular device, as seen in FIG. 6.

The image is focused, for an individual subject viewing the image through the ocular device, by adjusting the vertical position of the mirror with respect to the projector by the worm drive mechanism noted above. By moving the mirror assembly, the optical path between the object (either the fixed-position image, or the LED) and the corresponding Badal lens can be increased or decreased. As demonstrated in the discussion on the Badal principle above, this alters the placement of the focused image within the subject's eye. The mirror assembly can thus be positioned such that the projected image impinges on the retina of the subject's eye, bringing the image into focus.

A lens-mirror arrangement allowing dynamic range of focusing power of substantially between +6 diopters and -6 diopters is adequate to provide sharply-focused images for most of the general population.

Movable-image assembly 30 has a similar construction and operation. Briefly, with reference to the right-hand regions of FIGS. 6 and 7, an LED light source 170 in the image projector 132 produces an image directed against a pair of mirrors 174, 176 in mirror assembly 130, and reflected by a mirror 178 in the projector through a lens 186 along an optical pathway 32, where the image is viewed by the subject looking through the ocular device. The image is focused for the subject viewing the image, by adjusting the vertical position of mirror assembly 130, in a manner to be described. Each of the mirror assemblies described above is also referred to herein as focusing means.

In the embodiment shown, the optical pathlengths for both the fixed and movable images are equal, so that moving the mirrors coordinately, in the same direction and by the same distance, focuses both images simultaneously for the subject viewing the images. Accordingly, only a single focus adjustment, e.g., to focus the fixed-position image, is required.

Figure 8:
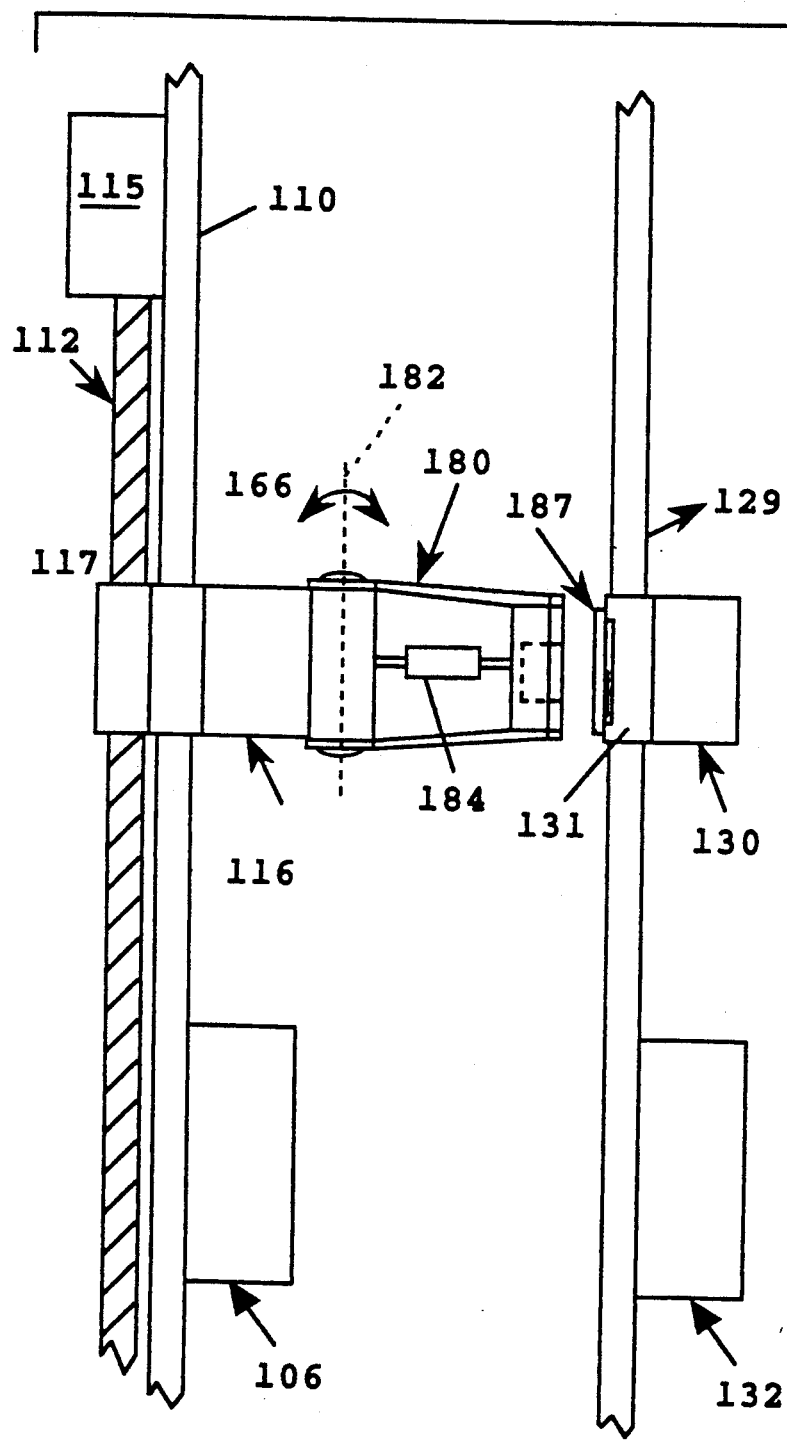
FIG. 8 is a side view of a tandem optical system according to one embodiment of the invention.
Figure 9A:
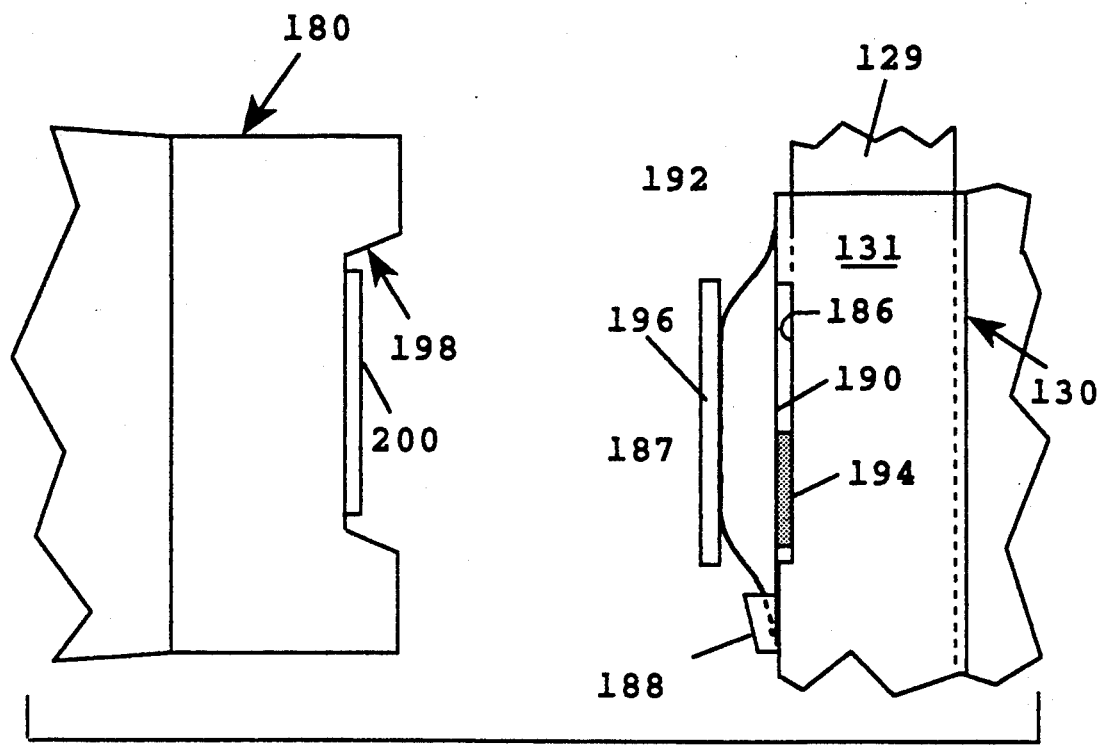
FIGS. 9A and 9B illustrate the coupling of the fixed-image and movable-image assemblies in the tandem optical system shown in FIG. 8.
Figure 9B:
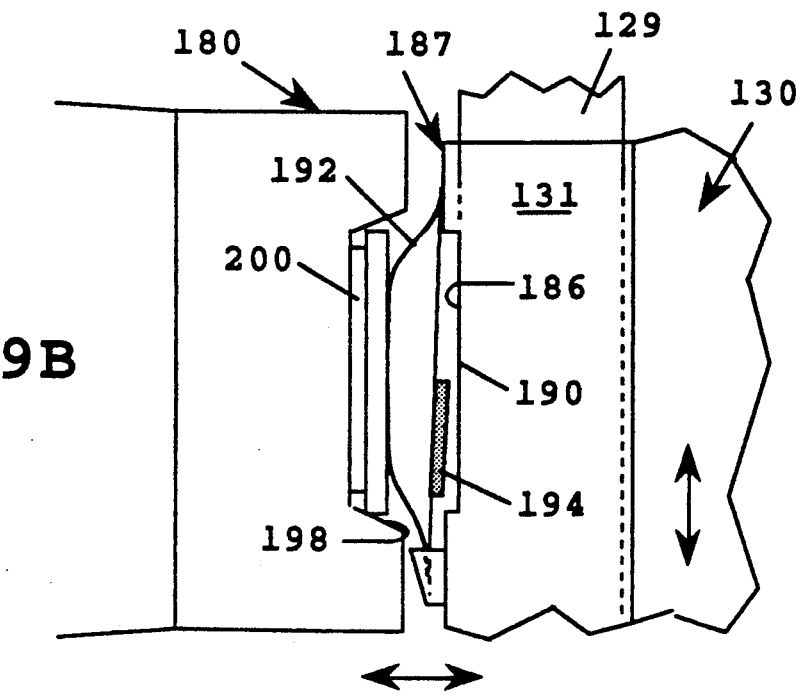

FIGS. 8, 9A and 9B illustrate details of a tandem optics system for use in focusing the fixed- and movable-image light assemblies coordinately, so that focusing the fixed-image assembly also serves to focus the movable-image assembly.

FIG. 8 shows portions of the two assemblies when aligned and positioned for focusing. Here secondary arm 129 in the stimulus arm is moved to a position of parallel alignment with frame arm 110 and the mirror assembly on the frame arm is moved by motor 115, acting through worm screw 112, to a position of vertical alignment with the mirror assembly on arm 129.

A coupling device 180 is carried on mirror assembly 116 for swinging about an axis 182 toward and away from a position of engagement with the movable position mirror assembly, as shown in FIG. 9B. The swinging movement is produced by activation of a solenoid 184 connecting the stationary and pivoting parts of the coupling device, as indicated.

Shown at the right in FIG. 9A is the sleeve region of mirror assembly 130 which is selectively positionable on arm 129. Sleeve 131 in assembly 130 has an elongate slot 186 which communicates with the surface of arm 129. A releasable brake structure 187 or means carried on the sleeve includes a spring 188 composed of inner and outer leaf-type spring members 190, 192, respectively. A brake pad 194 in the brake structure is carried on the inner side of member 190. Attached to the outer side of spring member 192 is a ferromagnetic plate 196.

Spring 188 is attached to sleeve 131 at its upper end in the figure and biased such that pad 194, which can extend through slot 186, is normally presser against the surface of arm 129, to hold the mirror assembly at a fixed vertical position on arm 129 as the arm is moved to selected positions.

Shown at the left in FIG. 9A is the right-hand region of coupling device 180 carried on the fixed-position image assembly. This region includes a notch 198 which is dimensioned to receive plate 196 snugly wherein, as shown in FIG. 9B. The notch and plate 196 on the brake structure form what is referred to herein, collectively, as registration means.

Located at the inner surface of the notch is an electromagnet 200 which can be energized when the coupling device is in its position of engagement.

When it is desired to adjust the focus of two image assemblies, the engagement arm is aligned with arm 110, and the two mirror assemblies are vertically aligned as noted above. The coupling device is then moved, by solenoid 184, to its position of engagement where the electromagnet in the coupling device is adjacent plate 196 in the brake structure. The electromagnet is then energized to clamp the plate to the magnet, drawing plate 196 into the registration notch, and causing the brake pad to be pulled out of the channel, and away from its contact with arm 129. At this point, the two mirror assemblies are vertically aligned, i.e., held in registry, by the immobilization of plate 196 in notch 198.

When the brake holding the mirror assembly in position on the arm is released, device 180 is vertically shifted, under the control of motor 115, to bring the fixed image into focus for the subject. The in-register coupling between the two mirror assemblies results in an identical vertical repositioning of mirror assembly 130, thus bringing the movable image into the subject's focus simultaneously with the fixed image.

After the focusing operation, the electromagnet is released, allowing mirror assembly 130 to lock at its new position, and the coupling device is swung back to its retracted position, out of the path of the movable-image assembly.

C. VISUAL-FIELD TESTING

To measure the extent of a subject's visual field using the above-described visual field analyzer requires (i) adjusting the mirror assemblies to obtain proper focus of the fixed-position and movable-position images, as viewed by a subject through the ocular device, (ii) displaying a series of transient images at different selected positions within the visual field of the subject, and (iii) recording the subject's response to the light stimuli.

The subject's responses are preferably recorded electronically, by a recorder 38 (FIG. 1). The recorder is typically connected to a hand switch which is operated by the user to indicate, in a yes/no manner, whether a particular transient image projected at a given position in the visual field was perceived. The recorder may include conventional software or other analytical algorithm means for determining, from the totality of responses, the limits of the field of vision of the subject, and/or the sensitivity of the subject to light in various field-of-vision regions. The latter tests may be conducted by altering the light intensity, color, or size of the transient image, as well as image position.

Alternatively, the apparatus may include an analyzer 40 which is designed to direct the position and/or intensity of the transient light image, based on the response of the subject, in a manner which optimizes the visual-field measurements being made. Automated analyzer systems for use in visual-field analysis have been described (Johnson, 1983b, Keltner), and these programs can be readily adapted to the apparatus of the present invention.

From the foregoing, it can be appreciated how various objects and features of the invention are met. The ocular device of the invention is lightweight, portable, relatively inexpensive, and can be used for extended periods without significant discomfort.

The Badal principle described above can be applied to visual field perimetry only in conjunction with the ocular device of the present invention. Current hemispherical surfaces, even if constructed in a semi-transparent manner as the invention, could not provide such a combination of a uniform background glow and image clarity because the present surfaces are so large, and placed so far from the subject's eye, that the eye would perceive the "speckled" nature of the surface. Hence, the fixation image and the stimulus image could not be clearly focused by such an arrangement. Thus, the placement of hemispherical surfaces in visual perimeters, as practiced in the prior art, inherently prevents the application of a Badal-type optical system. As a result, corrective lenses must be worn by those subjects having less than 20/20 vision when using prior art perimeters.

The tandem optical system provides a rapid and reliable method for coordinately focusing both fixed- and movable-image light assemblies, by a single focal adjustment. Further, the brake construction on the movable assembly can be made lightweight, to enhance the speed and accuracy of positioning of the movable assembly to selected test positions.

Although the invention has been described with reference to particular embodiments and methods, it will be appreciated that various changes and modifications can be made without departing from the invention.

It is claimed:

1. Apparatus for measuring a subject's response to a light stimulus, over the subject's visual field, comprising:
   an ocular device adapted to be placed over a subject's eye, including a transparent window defining an outwardly projecting, cavity-like inner surface dimensioned to encompass the subject's visual field in that eye,
   an optical system for producing a fixed-position image at one position in the subject's visual field, and a series of transient light images at different selected positions in the subject's visual field, and
   illuminating means for illuminating said surface to provide a substantially uniform glow on said inner surface, against which said fixed-position image and transient images may be perceived.

2. The apparatus of claim 1, wherein said illuminating means includes a light source adapted to direct light against said inner surface and a substantially uniform surface distribution of material on said window effective to produce such glow when illuminated.

3. The apparatus of claim 2, wherein said illuminating means is effective to provide a background light intensity of between about 5-15 candela/m$^2$.

4. The apparatus of claim 2, wherein said material is a speckle pattern of reflective spots on said window.

5. The apparatus of claim 2 wherein said material is a semi-transparent screen.

6. The apparatus of claim 2, wherein said material is a fluorescent or phosphorescent compound embedded in said window, and said light source is effective to produce fluorescent or phosphorescent emission of said compound, respectively.

7. The apparatus of claim 1, wherein said optical system is a Badal-type optical system.

8. The apparatus of claim 1, which further includes means for recording the response of the subject to said transient light image.

9. The apparatus of claim 8, which further includes program means operatively connected to said response means and to said test-image means to direct placement of such transient light images in response to the subject's response to previous transient light images.

10. A method for measuring a subject's response to a light stimulus, over the subject's visual field comprising
    placing over the subject's eye an ocular device having a transparent window defining an outwardly projecting, cavity-like inner surface dimensioned to encompass the subject's visual field in that eye,
    producing a fixed-position image at one position in the subject's visual field,
    producing a series of transient light images at different selected positions in the subject's visual field and, illuminating said surface to provide a substantially constant, uniform low on the surface against which said fixed-position image and such transient images may be perceived.

11. The method of claim 10, which further includes recording the response of the subject to said transient light images.

12. The method of claim 10, which further includes producing said transient light images at selected locations according to the response of the subjects to previous light images.

13. The method of claim 10, wherein said surface has a substantially uniform distribution of material which is effective to produce such glow when illuminated, and said illuminating includes directing a light against such surface.

14. The method of claim 10, wherein said illuminating includes directing a light against the inner surface of said inner surface, at an intensity effective to provide a background light intensity of between about 5-15 candela/m$^2$.

15. A tandem optical system for use in a visual testing of a subject comprising:
 (a) a frame arm;
 (b) a stimulus arm, which is movable in a three-dimensional region which is at a fixed distance from the subject;
 (c) fixed-image and movable-image assemblies carried on said frame arm and said stimulus arm respectively, each having (i) a light source and (ii) a focusing means which is movable with respect to said light source to change the focus of the light produced thereby as seen by the subject;
 (d) releasable brake means in the movable-image assembly for holding the light source and focus means at a fixed distance from one another when the brake is engaged, and allowing such distance to be changed when the brake is released;
 (e) a coupling device associated with said fixed-position image assembly for movement toward and away from a position of engagement with said brake means, including means for releasing said brake means at such points of engagement, and;
 (f) registration means associated with said fixed and movable image assemblies for maintaining the fixed-position and movable-position assemblies so that any change in the relative position of the light source and focus means of the fixed-position image assembly produces an identical change in the relative position of the light source and focus means of the movable-image assembly.

16. The system of claim 15, wherein said fixed-image and movable-image assemblies include Badal-type optics.

17. The system of claim 15, wherein the focusing means in said fixed-image and movable-image assemblies are slidably mounted on said frame arm, and stimulus arm, respectively.

18. The system of claim 15, wherein said brake means comprises a spring-loaded brake which in normally biased against the stimulus arm, to hold the focus means in movable-image assembly at a fixed-position in the stimulus arm.

19. The system of claim 18, wherein said brake means includes a ferromagnetic plate, and said coupling means includes an electromagnet which, when the coupling means is moved to its position of engagement, is effective to engage said plate magnetically, to move the spring-loaded brake away from its position in contact with the stimulus arm.

20. The system of claim 19, wherein said registration means includes a notch into which said plate is received, when said plate is engaged by said electromagnet.

* * * * *